US00PP12992P2

(12) United States Plant Patent
Zerr

(10) Patent No.: US PP12,992 P2
(45) Date of Patent: Sep. 24, 2002

(54) POINSETTIA PLANT NAMED 'FISCOR FIRE'

(75) Inventor: Katharina Zerr, Simmern (DE)

(73) Assignee: Floris AG, Binningen (CH)

( * ) Notice: Subject to any disclaimer, the term of this patent is extended or adjusted under 35 U.S.C. 154(b) by 0 days.

(21) Appl. No.: 09/496,201

(22) Filed: Feb. 2, 2000

(51) Int. Cl.[7] ..... A01H 5/00
(52) U.S. Cl. ..... Plt./307
(58) Field of Search ..... Plt./307

(56) References Cited

U.S. PATENT DOCUMENTS

PP9,347 P * 10/1995 Zerr ..... Plt./307
PP9,364 P * 11/1995 Zerr ..... Plt./307

OTHER PUBLICATIONS

Application for Plant Breeder's Rights, Germany, #EUP 213 (Nov. 9, 1998).
Application for Plant Breeder's Rights, Canada, #98–1531 (Nov. 25, 1998).
Application for Plant Breeder's Rights, Switzerland, #99–1485 (Jan. 13, 1999).

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct cultivar of Poinsettia plant named 'Fiscor Fire' characterized by having intense red bract color with an orange glow; medium-sized, flat involucre with moderately lobed bracts; intense dark-green foliage with weak lobes; compact and low, relatively wide plant habit; medium to early flowering response; and relatively good keeping quality of bracts and foliage.

1 Drawing Sheet

BACKGROUND OF THE INVENTION

The present invention relates to a new and distinct cultivar of Poinsettia plant known by the cultivar name 'Fiscor Fire', and botanically known as *Euphorbia pulcherrima*.

'Fiscor Fire' is a product of a mutation induction program carried out by the inventor, Katharina Zerr, in Hillscheid, Germany, in 1994. The primary objective of the induction program was to expand the bract color ranges of 'Fiscor' (U.S. Plant Pat. No. 9,364). 'Fiscor' is characterized by its relatively dark red-colored bracts, dark-green foliage and comparatively compact habit.

The irradiation program comprised exposing rooted cuttings taken from plants of the parent cultivar to an X-ray source of 30 Gy dosage in Ahrensburg, Germany, under the supervision of the inventor. The irradiated plants were grown out in a greenhouse in Hillscheid, Germany, and were asexually propagated by the inventor by taking cuttings. The plants resulting from these cuttings were screened for mutations as small, flowering, single-stem plants beginning in the fall of 1994. The mutations discovered were identified by numbers. Parts of plants exhibiting a mutation of interest were left to develop vegetative shoots which were used as cuttings and grown out.

'Fiscor Fire' originated from a single plant (No. 338) having intense orange-red bracts, which was discovered in the early summer of 1995. The plant, which was apparently completely mutated, was propagated vegetatively by taking cuttings, and the resulting plants were screened for uniformity in spring of 1996 prior to further propagation. The clone was examined more closely during 1997, when it was compared to its parent variety 'Fiscor'. Horticultural examination of the clone starting in 1998 and continuing thereafter has confirmed that the combination of characteristics as herein disclosed for 'Fiscor Fire' are firmly fixed and retained through successive generations of asexual reproduction.

BRIEF DESCRIPTION OF THE INVENTION

The following traits have been repeatedly observed and are determined to be basic characteristics of 'Fiscor Fire' which in combination distinguish this Poinsettia as a new and distinct cultivar:

1. Intense red bract color with an orange glow;
2. Medium-sized, flat involucre with moderately lobed bracts;
3. Intense dark-green foliage with weak lobes;
4. Compact and low, relatively wide plant habit;
5. Medium to early flowering response; and
6. Relatively good keeping quality of bracts and foliage.

'Fiscor Fire' has not been observed under all possible environmental conditions. The phenotype may vary significantly with variations in environment such as temperature, light intensity, and daylength without any change in genotype. The following observations, measurements and comparisons describe plants grown in Langley, British Columbia, Canada, under greenhouse conditions which approximate those generally used in commercial practice.

Of the many commercial cultivars known to the inventor, the most similar in comparison to 'Fiscor Fire' is the parental cultivar 'Fiscor'. In comparison to 'Fiscor', 'Fiscor Fire' has a brighter bract color with a more orange-red hue, less intense anthocyanin coloring of the stem and less intense red petioles. The finishing time for 'Fiscor Fire' is the same or slightly shorter than for 'Fiscor'.

BRIEF DESCRIPTION OF THE DRAWING

The accompanying color photographic illustration shows typical inflorescence and foliage of a mature potted plant of 'Fiscor Fire', with colors being as true as possible with illustrations of this type.

DETAILED BOTANICAL DESCRIPTION

The plants described were grown in a greenhouse in Langley, British Columbia, Canada, in the fall of 1998. Rooted cuttings were planted into 15-cm pots on August 10, and were pinched on August 20, leaving 8 nodes. The minimum temperature was 23° C. until October 10, 20° C. to mid-November, and lower thereafter. The plants initiated flowers under natural short-day conditions in the fall.

Observations and measurements of 15 week old plants, after planting of rooted cuttings, were mainly taken at the beginning of full flowering. In the following description, color references are made to The Royal Horticultural Society (R.H.S.) Color Chart. The color values were determined indoors in a north light.

Classification:

*Botanical.*—*Euphorbia pulcherrima*.

*Commercial.*—Poinsettia cv. 'Fiscor Fire'.

Parentage: Induced mutation of 'Fiscor'.

Plant:

*Form.*—Shrub, self-branching.

*Growth habit.*—Moderately compact under natural light conditions in fall, weak to medium growth, pinched plants are bushy and relatively wide.

*Height* (*including* 12 *cm high pot*).—Approximately 39.9 cm.

*Width.*—54.3 cm.

*Average number of branches.*—8.7.

*Average number of inflorescence.*—8.0.

*Stem color.*—Light to medium green, RHS 143A to 144A, with weak infusion of anthocyanin, brownish RHS 176B.

*Peduncle.*—Light green, RHS 143C, about 6 mm long.

*Rooting.*—Medium, sufficiently rooted for transplanting after about 20 days in a greenhouse at a temperature of 22–24° C.

*Blooming habit.*—Flowering response time under natural short day conditions in autumn: botanically (cyathia open) — around December 1; commercially (bracts colored, marketable) — in late November.

*Flowering response time.*—About 9 to 9.5 weeks.

Foliage:

*Shape.*—Broad elliptical, with rounded or slightly acute base, weak lobes and acuminate tip.

*Edge of margin.*—Entire.

*Texture.*—Upper surface: Smooth, flat and only weakly veined, color of veins is about RHS 146D or lighter; the basal part of the midrib has only little reddish coloring, like the petiole, though weaker. Lower surface: Flat and smooth except for the slightly protruding midrib and finer side veins, which are arranged in a pinnate pattern; the vein color is light green, RHS 145C.

*Size.*—Leaf blade length is 12.5 cm; leaf blade width is 8.4 cm; petiole length is 7.5 cm.

*Color.*—Generally a uniform dark green. Mature foliage: upper surface is RHS 139A. under surface is RHS 137B. New foliage: upper side is about RHS 143A. under side is about RHS 137D.

*Petiole color.*—Red to dark-red, near RHS 53B.

*Aspect.*—Petioles and leaves are mainly horizontally directed.

*Disease resistance.*—Typical, no special observations made.

Flowering description:

*Whole inflorescence.*—Almost flat and horizontally directed with the bracts in an overlapping arrangement and with a tight center already at the beginning of flowering.

*Keeping quality.*—Relatively good.

*Number of bracts per inflorescence.*—7–9.

*Diameter of inflorescence.*—25 cm.

*Size of bract.*—Largest true bract is 13.7 cm long and 8.6 cm wide; petiole is 1.8 cm.

*Bract shape.*—Ovate, with rounded base, acuminate tip, and with weak lobes; the smaller, younger bracts are broad elliptically shaped and usually without lobes.

*Bract texture.*—Flat and smooth, almost no rugosity; the veins are arranged in a pinnate pattern and are hardly visible on the upper surface. The color of the veins corresponds to the bract color or appears slightly darker, while the veins on the lower surface are usually lighter; brownish-pink, about RHS 47B or lighter.

*Bract color.*—Generally a deep orange-red; uniform and without fading near the margin. Upper surface: Near RHS 44A. Lower surface: RHS 45B–C.

*Secondary bract.*—Broad-elliptical shape, round to acute base, no lobes or very weak lobes, margin entire; upper surface near RHS 44A, and lower surface RHS 45B–C; largest secondary bract about 9.5 cm long, 6 cm wide.

*Petiole color.*—Red, about RHS 45A.

*Cyathia.*—Few, about 10 in a narrow cluster, about 25 mm wide. Diameter of the single cyathium 6 mm. Color: Mainly light green, RHS 143C, with medium-green patches, about RHS 137D; top is red, near RHS 44A. Retention of the mature cyathia: About 2 weeks, depending on growing conditions. Nectar Cups: One nectar cup per cyathium, medium sized, 5–6 mm diameter, 4 mm length, golden yellow, RHS 12A, usually no anthocyanin coloring near margin.

Reproductive organs:

*Stamens.*—About 20; red filaments, RHS 45A, fertile, yellow pollen, RHS 12A.

*Pistils.*—One per cyathium, style and stigma are red, RHS 45A; 6-lobed, trifurcate stigma.

*Ovaries.*—Triangular, 3 ovules.

Fruit/seed set: No observations made.

I claim:

1. A new and distinct poinsettia plant named 'Fiscor Fire', substantially as illustrated and described.

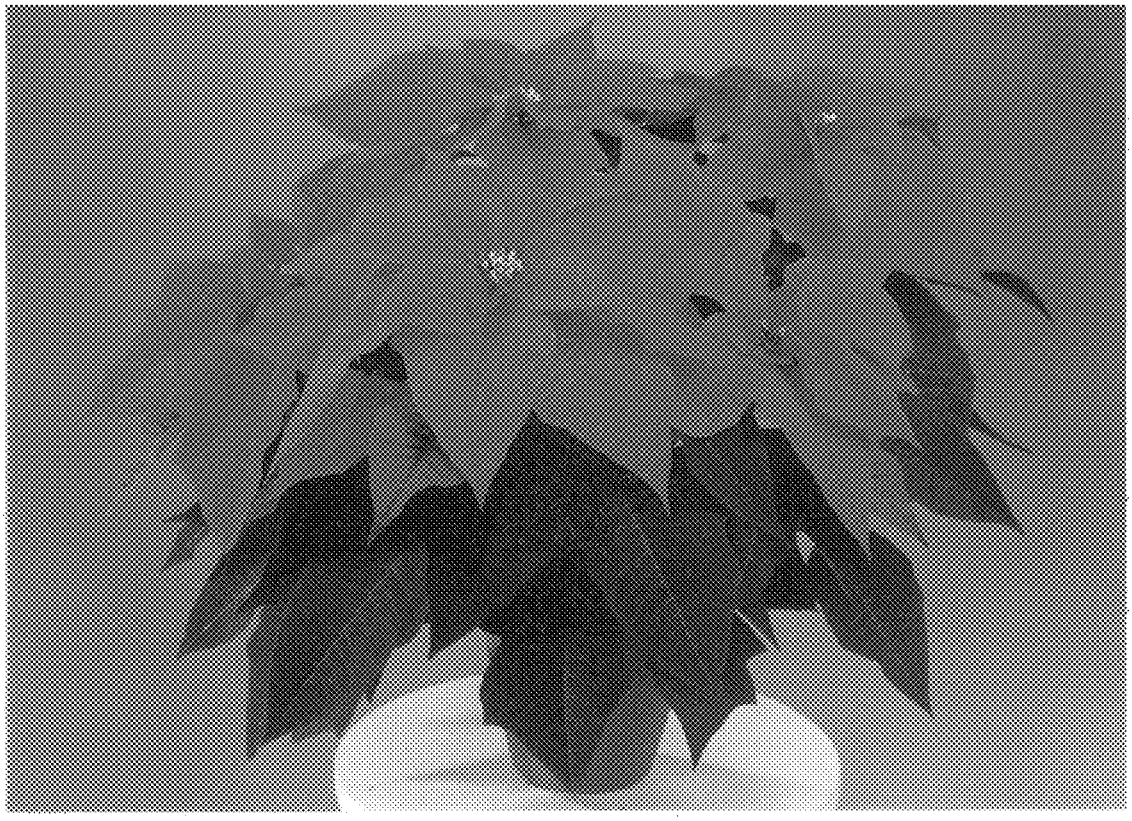

* * * * *